United States Patent [19]

Cattani

[11] Patent Number: 4,710,209

[45] Date of Patent: Dec. 1, 1987

[54] MOISTURE TRAP FOR FLUID SUCTION EQUIPMENT, IN PARTICULAR AS EMPLOYED IN DENTISTRY

[75] Inventor: Augusto Cattani, Parma, Italy

[73] Assignee: Officine Agusto Cattani & C. S.p.A., Parma, Italy

[21] Appl. No.: 876,271

[22] Filed: Jun. 19, 1986

[30] Foreign Application Priority Data

Jul. 31, 1985 [IT]  Italy ................. 40080 A/85

[51] Int. Cl.⁴ .................. B01D 45/16; B01D 45/08; B01D 51/00
[52] U.S. Cl. ........................ 55/418; 55/426; 55/436; 55/446
[58] Field of Search ....... 55/257 QV, 257 NP, 257 R, 55/225, 226, 446, 308, 418, 426, 436

[56] References Cited

U.S. PATENT DOCUMENTS

| | | | |
|---|---|---|---|
| 2,252,174 | 8/1941 | Glab | 55/257 NP X |
| 2,290,323 | 7/1942 | Graham | 55/436 |
| 2,632,523 | 3/1953 | Stephens et al. | 55/257 NP |
| 3,119,675 | 1/1964 | Gallagher | 55/257 QV |
| 3,284,064 | 11/1966 | Kolm et al. | 55/418 X |
| 3,969,094 | 7/1976 | Dunson, Jr. et al. | 55/257 R |
| 4,225,326 | 9/1980 | Hummel et al. | 55/257 R |

FOREIGN PATENT DOCUMENTS

| | | | |
|---|---|---|---|
| 701289 | 1/1965 | Canada | 55/257 QV |
| 237992 | 8/1925 | United Kingdom | 55/257 NP |
| 388764 | 11/1973 | U.S.S.R. | 55/226 |
| 797739 | 1/1981 | U.S.S.R. | 55/257 R |

Primary Examiner—Kathleen J. Prunner
Attorney, Agent, or Firm—Darby & Darby

[57] ABSTRACT

A moisture trap is disclosed of the type, used in fluid suction equipment for dentistry in particular, which comprises a negative pressure intake (1) consisting of a venturi (2) that draws in fluid and delivers it into a vertical separation chamber (3) having an outlet (6) at bottom via which liquids are discharged, and an outlet (7) uppermost via which air is exhausted. A trap according to the invention has a separator device, located between the chamber fluid inlet (9) and the air outlet (7), embodied as a column of components arranged in such a way as to create a tortuous passage through the separation chamber (3) in which the direction of the stream of fluid is changed several times.

4 Claims, 4 Drawing Figures

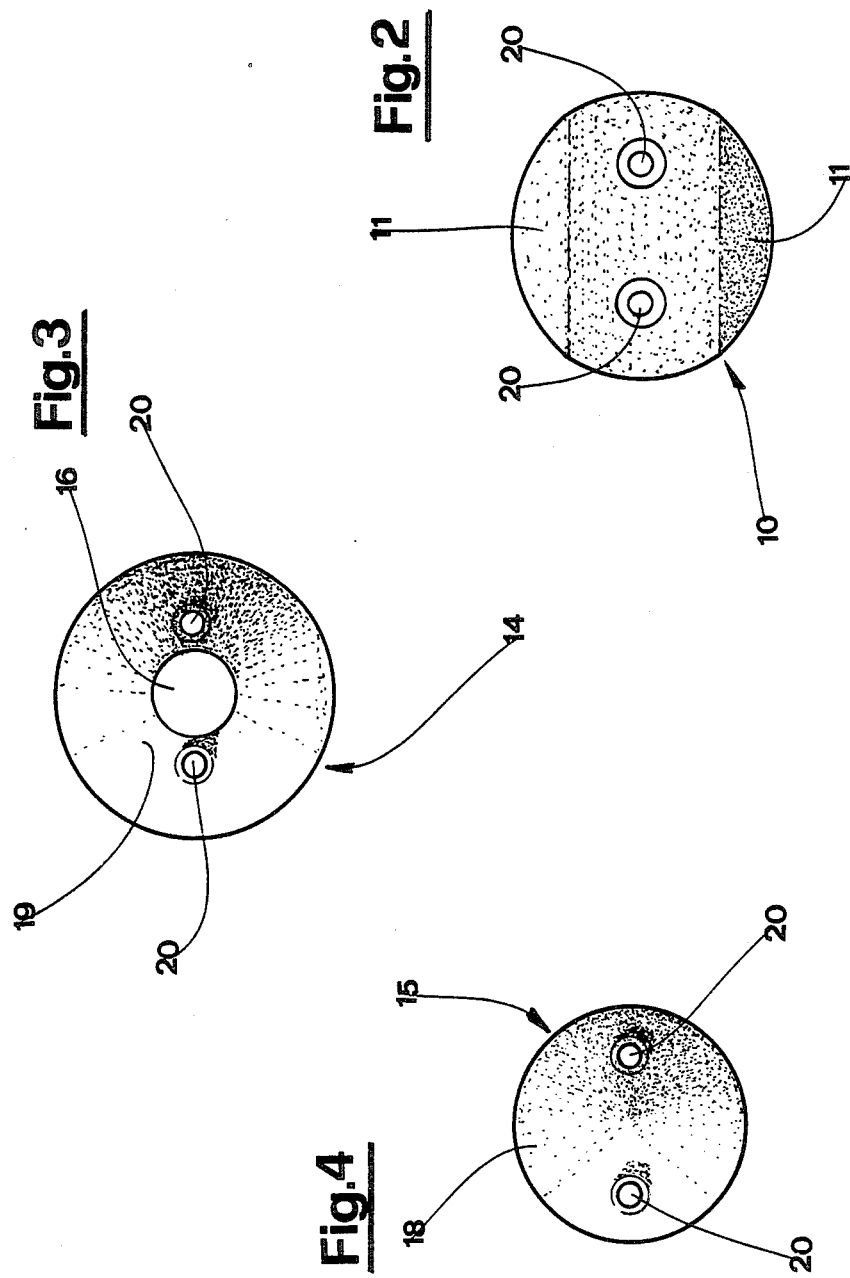

MOISTURE TRAP FOR FLUID SUCTION EQUIPMENT, IN PARTICULAR AS EMPLOYED IN DENTISTRY

BACKGROUND OF THE INVENTION

The invention described herein relates to a moisture trap for the separation of liquid from air, intended for fluid suction equipment such as is used in dentistry, in particular.

Such a device is of the type that employs a negative pressure intake, essentially a venturi duct, which draws in fluid consisting of air and liquid and delivers it into a vertical separation chamber. The chamber has an outlet at bottom through which a preponderance of liquid matter is discharged, and an outlet at the top through which a preponderance of air is exhausted.

It is difficult to obtain a thorough separation in moisture traps of the type, inasmuch as part of the liquid will be entrained by the airstream in the separation chamber, and discharged through the air outlet in the form of droplets.

Attempts have been made to overcome such a drawback by providing filters downstream of the air outlet located at the top of the separation chamber. There are drawbacks with such an expedient, however, since the need arises for regular, systematic servicing of the filters in order to avoid the ever-present hazard of blockage. What is more, installation of a filter at the air outlet of a separation chamber can reduce the effectiveness of suction equipment considerably, as a result of unwarranted backpressure being set up downstream of the intake device, i.e. the venturi.

Another drawback that can be encountered with suction equipment is that of gurgling through the drain into which the liquids are discharged.

The overriding object of the invention is that of obviating the drawbacks mentioned above.

SUMMARY OF THE INVENTION

The signal advantages of simplicity in construction, dependability, highly efficient operation, and other advantages besides, are realized with a moisture trap according to the invention; such a trap is of the type intended for fluid suction equipment, in particular as employed in dentistry, comprising a negative pressure intake embodied as a venturi duct that draws in fluid and delivers it into a vertical separation chamber having a bottom outlet through which a preponderance of liquid is discharged, and a top outlet through which a preponderance of air is exhausted. The trap disclosed incorporates at least one separator device located internally of the separation chamber at a position intermediate of the fluid inlet section, located at bottom, and the outlet from which air is exhausted, located uppermost, for the purpose of trapping liquid entrained by the airstream, predominantly in the form of droplets, and causing its return toward the discharge outlet at bottom of the chamber.

BRIEF DESCRIPTION OF THE DRAWINGS

The invention will now be described in detail, by way of example, with the aid of the accompanying drawings, in which:

FIG. 2 is the section through I—I in FIG. 1, seen in enlarged scale;

FIG. 3 is the section through II—II in FIG. 1, seen in enlarged scale;

FIG. 4 is the section through III—III in FIG. 1, seen in enlarged scale.

DESCRIPTION OF THE PREFERRED EMBODIMENT

Figure 1:
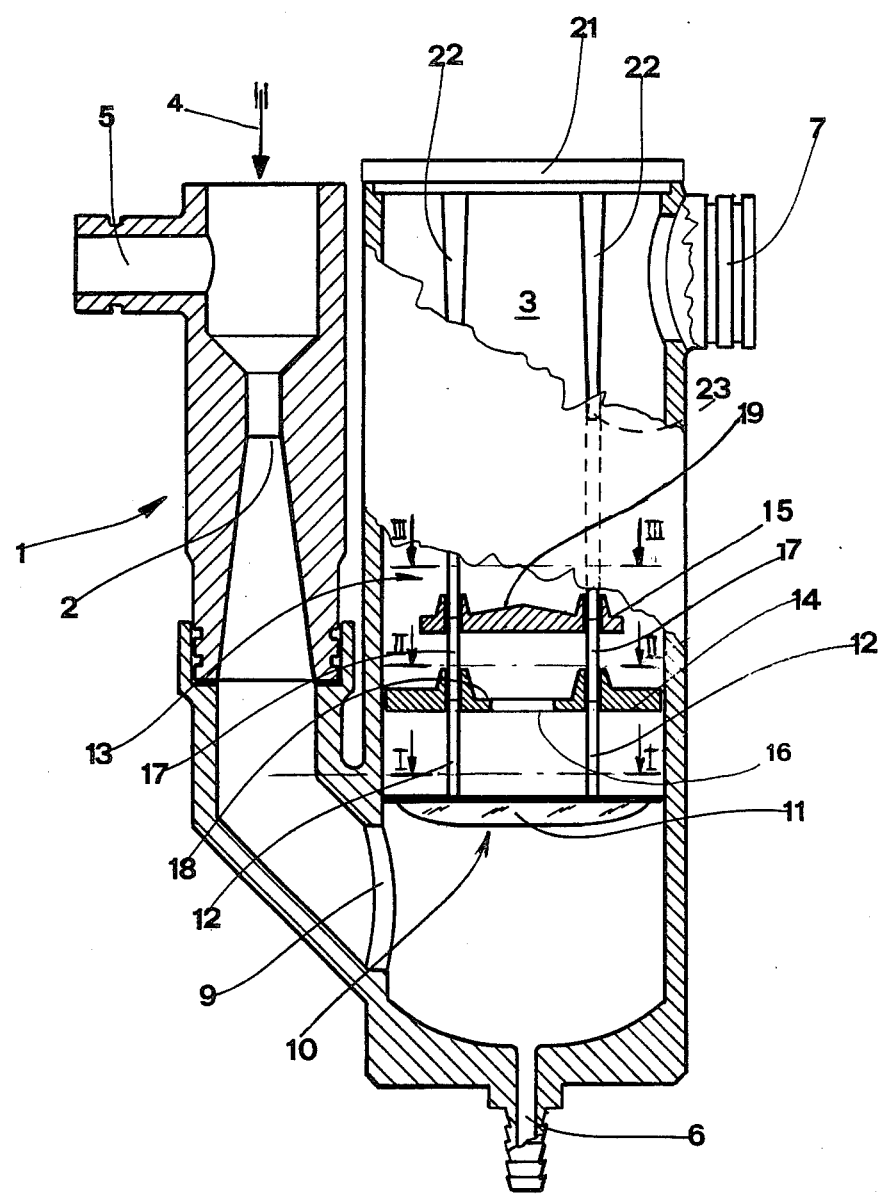
FIG. 1 is a schematic representation of the moisture trap, seen in section through a vertical plane.

With reference to the drawings, 1 generally denotes a negative pressure intake that takes the form of a venturi duct 2; fluid drawn in is delivered by the outlet of the venturi into a cylindrical and vertically disposed separation chamber 3.

The negative pressure intake is operated by a stream of air 4 generated through the venturi 2. Fluid is drawn in by way of an inlet 5 and mingles with the airstream 4 inside the venturi, the outlet of which connects with the lower end of the separation chamber 3.

The separation chamber is provided with an outlet 6 at bottom, through which liquids are discharged, and with a further outlet 7 uppermost, via which air is exhausted.

According to the invention, the separation chamber 3 is provided at a given point intermediate of the inlet section 9, where fluid enters the chamber, and the outlet 7, via which air is exhausted, with a separator device; the purpose of such a device is to trap such liquid as is carried upward, entrained in the airstream, and cause its return toward the bottom outlet 6.

The device comprises a separator baffle 10 located immediately above the inlet section 9 in such a way as to enclose the chamber 3, in part, while affording free passage only at the two opposite sides occupying positions on either flank of the stream of fluid entering the inlet section.

More precisely, the separator baffle 10 is embodied as a disk having two edges 11 bent downward at the two opposite sides in question. The essential purpose of the separator baffle 10 is to provide a barrier to the progress of liquid projected upwards by the vortex that is set up in the stream of fluid at the lower end of the separation chamber 3, i.e. at the inlet section 9.

Located above and at a predetermined distance from the separator baffle 10, one has a column separator, generally denoted 13, consisting in a plurality of components arranged one above the next at predetermined mutual distances.

Such a plurality of components is embodied utilizing two types of disk, denoted 14 and 15, installed one above the other in alternation so as to create the column.

The disk denoted 14 is of dimensions such as to mask off the peripheral part of the cross sectional area of the separation chamber 3, affording a passage at center only. 16 denotes the hole located centrally in the disk 14. By contrast, the disk denoted 15 is of dimensions such as to mask off the central part of the cross sectional area of the separation chamber 3, affording a passage at the periphery.

Both the disks 14 and 15 thus embodied are aligned with the axis of the separation chamber 3; accordingly, a stream of fluid rising through the chamber will be afforded passage only by way of the hole 16 at the column center, in the case of the disk denoted 14.

The disk denoted 15, on the other hand, allows fluid to pass only by way of the annular area adjoining the cylindrical wall of the chamber 3. The dimensions of the two disks 14 and 15 are such, furthermore, that the hole 16 in the center of the one disk 14 will be masked completely by the remaining disk 15.

The disks 14 and 15 are thus arranged in alternation at given distance one from the next, forming a column, and fluid rising through the separation chamber 3 is obliged to follow a tortuous route, with frequent changes in direction, in finding its way through the areas affording a passage. The end result is that such droplets of liquid as are entrained in the rising stream of fluid will be trapped, coming up as they must against the surfaces of the disks 14 and 15, so that the stream of fluid remains substantially free from droplets of liquid on arrival at the top of the column.

The droplets of liquid trapped are directed downward toward the chamber outlet 6, and to this end, the top surface 18 of each centerless disk 14 is pitched inward toward the center hole 16; thus, any droplets falling on the top surface 18 will trickle toward the hole 16 and drop into the disk beneath 15, the top surface 19 of which is pitched away toward the periphery, creating a generally convex surface with its highest point at center. Droplets forming on the top surface 19 in questions are therefore obliged to run away down toward the periphery of the disk 15.

The disks 14 and 15 and the baffle 10 are aligned with the axis of the separation chamber 3 and set apart at predetermined distances one from the next. More exactly, the separator baffle 10 is connected to the bottom disk 15 of the column separator 13 by way of distance pieces 12. The disks 14 and 15 are interconnected and held in position, with respect both to each other and to the axis of the column separator, by further distance pieces 17. The distance pieces denoted 17, issuing from the respective top surface 18 and 19 of each disk 14 and 15, exibit top ends that are proportioned so as to locate in corresponding sockets 20 provided in the underside of the single disk above. Thus, by locating each distance piece 17 in a corresponding socket 20, one achieves correct spacing of the disks 14 and 15 one from the next, as well as alignment of all the disks in relation to the axis of the column.

The disks 14 and 15 might be held together either by fastening the ends of the distance pieces 17 to the sockets 20 directly, or by utilizing other fastening means such as tie rods, for instance, inserted in clearance holes bored through the sockets 20 and the distance pieces 17, serving to clamp the entire column assembly through an axial direction.

The disks 14 and 15 of the column assembly are made fast to the lid 21 of the separation chamber 3 by means of rods 22 the ends of which offer sockets 23 in which to locate the ends of the distance pieces 17 issuing from the uppermost disk of the column.

Thus embodied, the entire separator device can be withdrawn from and located in the separation chamber 3 simply by removing and refitting the lid 21.

With a trap according to the invention, one achieves total separtion of liquid from the stream of fluid rising through the separation chamber 3, practically considered, without giving rise to any appreciable pressure loss in the airstream.

What is claimed:

1. A moisture trap for separating liquid and air from a fluid suspension of air and liquid, for use with fluid suction dental equipment, comprising:
    a generally cylindrical, vertical separation chamber for separating liquid and air from a fluid suspension fo air and liquid, sealed by a concave interior bottom wall and a top wall including a removable flanged lid, said chamber having an inlet located at a lower portion of the cylindrical sidewall of said chamber, a liquid outlet located at the lowest level of said concave interior bottom wall, and an air outlet located at an upper portion of the cylindrical sidewall opposite said inlet;
    an intake for a fluid suspension of air and liquid including a venturi duct, said intake in fluid communication with said inlet;
    a circular separator baffle disk having opposite edges bent downward, said disk positioned within said separation chamber to substantially block said chamber above said inlet;
    a circular peripheral baffle disk having a central opening, said peripheral baffle positioned above said separator baffle disk within said separation chamber;
    a circular core baffle disk having an outside diameter smaller than said peripheral baffle disk, said core baffle disk positioned above said peripheral baffle disk within said separation chamber; and
    mounting means for securing said baffle disks to each other at a fixed distance and relative orientation, said mounting means secured to said removable flanged lid to secure said disks at a fixed position within said separation chamber.

2. Moisture trap as in claim 1, wherein said mounting means includes distance pieces that ensure the correct positioning of said baffle disks one in relation to the other, and their correct alignment with respect to the axis of the separation chamber.

3. Moisture trap as in claim 2, wherein the distance pieces extend from the top surface of each baffle disk and exhibit top ends that are proportioned so as to locate in corresponding sockets provided in the underside of the single baffle disk above.

4. Moisture trap as in claim 1, wherein the top surface of said peripheral baffle disk is pitched toward the central opening that affords passage, and the top surface of said core baffle disk exhibits a generally convex profile with its highest point at center.

* * * * *